United States Patent [19]

Shimizu et al.

[11] Patent Number: 5,301,440
[45] Date of Patent: Apr. 12, 1994

[54] ON-LINE TYPE MOISTURE MEASURING SYSTEM FOR POWDERED OR GRANULAR MATERIALS

[75] Inventors: Motoharu Shimizu; Osamu Maisui, both of Osaka, Japan

[73] Assignee: Kabushikikaisha Matsui Seisakusho, Osaka, Japan

[21] Appl. No.: 901,982

[22] Filed: Jun. 22, 1992

[30] Foreign Application Priority Data

Jun. 27, 1991 [JP] Japan .................................. 3-183816

[51] Int. Cl.$^5$ .............................................. F26B 19/00
[52] U.S. Cl. ............................................ 34/89; 34/54; 34/168
[58] Field of Search ............... 34/89, 57 R, 57 A, 168, 34/54, 56, 46, 48, 50, 44, 36

[56] References Cited

U.S. PATENT DOCUMENTS 5,146,692  9/1992  Ogiri et al. ............................... 34/36

Primary Examiner—Henry A. Bennett
Attorney, Agent, or Firm—Jones, Tullar & Cooper

[57] ABSTRACT

An on-line type moisture measuring system for powdered or granular materials wherein the moisture content of the materials is repeatedly measured by supplying a dehumidified and dried air each time the materials are sampled for measuring and thereafter automatically discharged. The system is comprised of a combination of sampling means and a moisture measuring apparatus. The sampling means samples a fixed amount of the materials from a material storage container and pneumatically transports the sampled materials. The moisture measuring apparatus includes dehumidified and dried air supply means for heating, dehumidifying and supplying air, material weighing means for weighing the sampled materials, a vaporization treatment chamber having an airtight vaporizer with a heater in which the materials received in a sample boat are heated while the dehumidified and dried air is fed as a carrier gas, a moisture measuring chamber including a moisture meter for measuring the water quantity of the materials based on the reaction of a Karl Fischer reagent by receiving the vapor generated in the vaporizer together with the carrier gas, and an arithmetic operation unit for calculating the moisture content of the sampled materials based on the water quantity measured by the moisture measuring chamber and the weight value measured by the material measuring means.

4 Claims, 14 Drawing Sheets

ON-LINE TYPE MOISTURE MEASURING SYSTEM FOR POWDERED OR GRANULAR MATERIALS

BACKGROUND OF THE INVENTION

1. Background of the Invention

The present invention is related to an improvement of an on-line moisture measuring apparatus wherein powdered or granular materials including inorganic materials such as pelletized resins and ceramics are automatically sampled and the moisture content thereof is automatically measured.

2. Prior Art

Generally, keeping moisture content of resin materials constant in order to maintain good quality of the resin products created a most important problem because with an inappropriate moisture content of the resin materials to be supplied into a molding machine defects such as a silver line or void are caused. Therefore, resin materials are usually dried by the use of a hopper dryer prior to being supplied into the molding machine. However, before the resin materials are fed into the hopper dryer, they are apt to absorb moisture in the air while being stored in a silo or a tank of intermediate stage for a fixed period of time after a kraft bag or a flexible container which is used to carry resin materials is opened. Accordingly a fixed heating temperature and a fixed heating time are set for the hopper dryer, which are based on an estimated moisture content of the resin materials. But such a conventional method for drying resin materials by the use of a hopper dryer leaves further room for improvement in saving labor.

On the other hand, a titration analysis using a Karl Fischer reagent has been conventionally known as a method for titrating and analyzing the moisture content of resin materials. A moisture meter has been developed in which titration analysis by a Karl Fischer reagent is performed by means of a coulometric method, a volumetric method, and a colorimetric method, whereby a high accuracy can be obtained.

Considering the above, an on-line moisture control method and the system has been proposed by the present inventors in JP-A-3-63558 (U.S. patent application Ser. No. 557,865 now U.S. Pat. No. 5,146,692 and EPC Patent Publication 0411848) wherein powdered or granular materials such as resin materials are automatically sampled and their moisture content is measured by means of a Karl Fischer reagent employing inert gas as a carrier gas.

However, the invention employed inert gas such as nitrogen gas as a carrier gas for a Karl Fischer reagent. Therefore, a gas cylinder containing inert gas should be regularly exchanged and pipings were increased and complexed. Furthermore, a gas cylinder should be frequently exchanged when the system was used many times and consequently the consumption of inert gas increased. Therefore, the invention leaves further room for improvement from the view point of maintenance.

SUMMARY OF THE INVENTION

The present invention is proposed to solve the above-mentioned problems and an object of the present invention is to provide an on-line moisture measuring system wherein maintenance is facilitated by eliminating exchange of gas cylinders.

One of an on-line moisture measuring system according to the present invention is provided with sampling means designed to be attached to a material storage container storing powdered or granular materials for sampling a fixed amount of the materials and for pneumatically transporting the sampled materials, dehumidified and dried air supply means having an air supply source for generating dehumidified and dried air by heating and dehumidifying the air supplied from the air supply source, material weighing means for weighing the sampled materials fed from the sampling means, and a vaporization treatment chamber including an airtight vaporizer with a heater and having a sample boat for receiving the materials weighed by the material weighing means. The airtight vaporizer heats the weighed materials received in the sample boat while receiving the dehumidified and dried air supplied from the dehumidified and dried air supply means as a carrier gas. The on-line moisture measuring system is also provided with a moisture measuring chamber including a moisture meter for measuring the moisture quantity of the weighed materials by the reaction of a Karl Fischer reagent by receiving the vapor generated in the vaporizer together with the carrier gas. The on-line moisture measuring system is further provided with an arithmetic operation unit for calculating the moisture content of the sampled and weighed materials based on the moisture quantity measured by the moisture measuring chamber and the weight value weighed by the material measuring means. In the present invention a fixed amount of powdered or granular materials sampled from the material storage container is repeatedly supplied each time the sampled materials are treated in the vaporization treatment chamber so as to get the moisture content of the sampled materials.

Another on-line moisture measuring system according to the present invention is further comprised of a communication passage communicating the vaporization treatment chamber and the moisture measuring chamber, and an air purge means for purging the dehumidified and dried air supplied from the dehumidified and dried air supply means from both the vaporization treatment chamber and the moisture measuring chamber respectively into atmosphere.

In still another on-line moisture measuring system according to the present invention, transportation of the sampled materials into the vaporization treatment chamber is performed by the dehumidified and dried air supplied from the dehumidified and dried air supply means is used as a transport air.

Following functions are fulfilled according to the present invention.

Sampled powdered or granular materials are fed from the material storage container, weighed by the material weighing means, received in the sample boat, carried in the vaporization treatment chamber, and heated therein. Under heat treatment process, the carrier gas which is dehumidified and dried so as to have a low dew point is fed into the moisture measuring chamber side in the vaporization treatment chamber from the dehumidified and dried air supply means. The moisture discharged from the heated powdered or granular materials in the form of a vapor is fed into the moisture measuring chamber together with the carrier gas.

Moisture measurement by means of a Karl Fischer reagent is performed in the moisture measuring chamber. The measured water quantity is sent to the operation unit together with the weight value measured by the material weighing means. In the operation unit the moisture content of the materials is calculated, sample data such as the data and time of sampling and a sample port number are output, and they are recorded and stored.

After the sampled powdered or granular materials are heated in the vaporization treatment chamber, the sample boat is taken out of the vaporizer and the heated materials on the sample boat are discharged.

According to the on-line moisture measuring apparatus of the present invention, powdered or granular materials are automatically sampled, fed into the vaporization treatment chamber, heated therein, measured their moisture content, and automatically discharged after the moisture measurement is finished. In the same manner as mentioned above, sampling, heat treatment, moisture measurement and discharge of powdered or granular materials can be repeated unmanned.

DETAILED DESCRIPTION OF THE INVENTION

Embodiments of the present invention will be described referring to the attached drawings.

Figure 1:
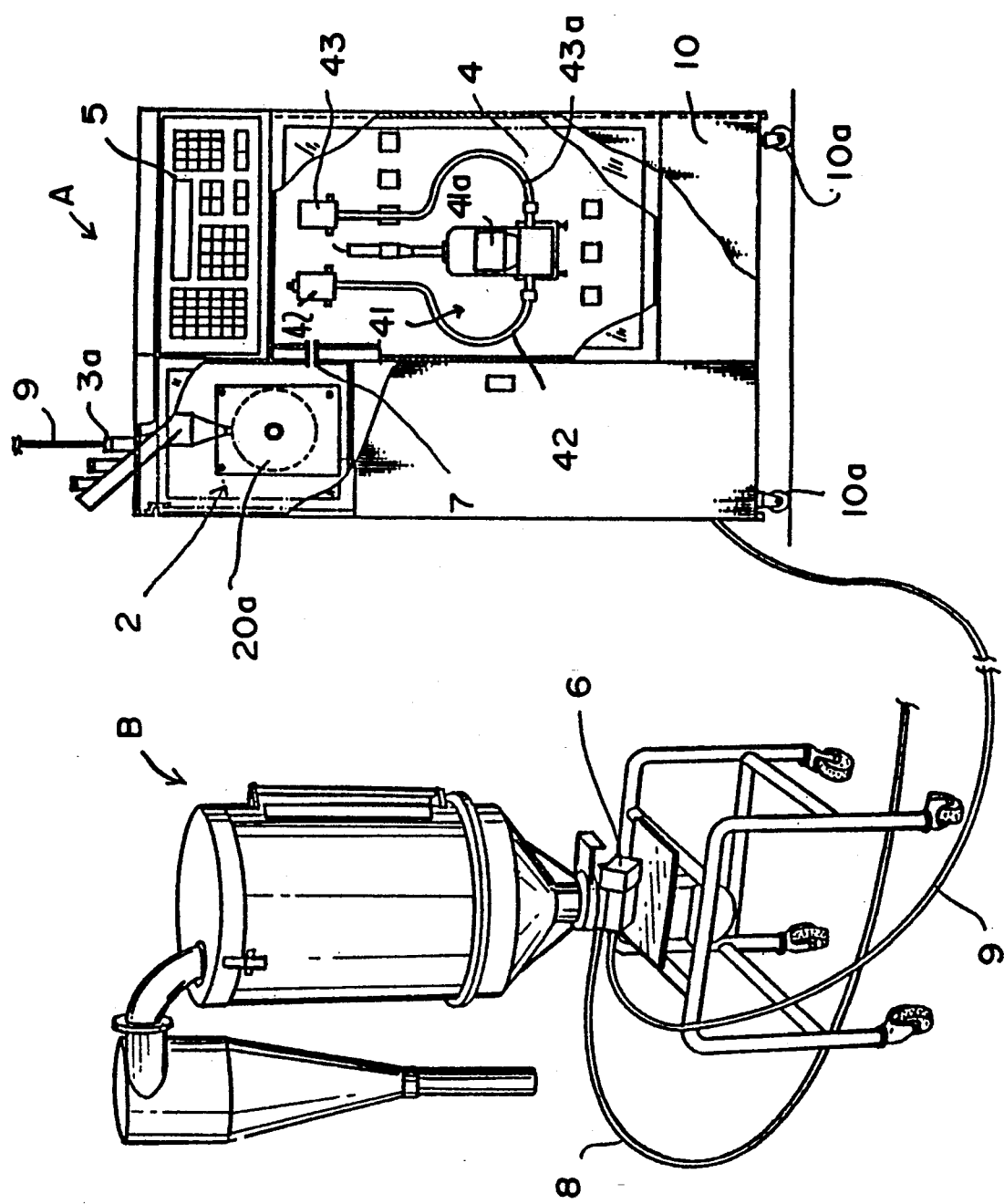
FIG. 1 is a schematic view of an on-line moisture control system employing a moisture measuring apparatus of the present invention.

FIG. 1 is a schematic view of an on-line moisture control system for pelletized resins employing an on-line moisture measuring apparatus of the present invention.

A main body 10 of a moisture measuring apparatus A includes a vaporization treatment chamber 2 containing a vaporizer 20a which heats sampled and weighed pelletized resins (not shown) and extracts water from the pelletized resins in the form of a vapor while a carrier gas dehumidified and dried to have a low dew point is supplied. The main body 10 of the moisture measuring apparatus A also includes a moisture measuring chamber 4 containing a moisture meter 41 which measures the water quantity of the pelletized resins by reacting the extracted water and the carrier gas with a Karl Fischer reagent. Casters 10a, 10a are provided under the main body 10 for conveying the main body 10. Dehumidified and dried air supply means 1 (see FIG. 2) provided in the moisture measuring apparatus A supplies dehumidified and dried air through an air supply pipe 8 toward sampling means 6 provided at the bottom of a hopper dryer (a material storing container B) storing pelletized resins. Consequently a fixed amount of pelletized resins is sampled and automatically fed into the vaporization treatment chamber 2 through sample ports 3a provided as material insert ports at the top of the vaporization treatment chamber 2 in the moisture measuring apparatus A. The numeral 5 indicates a display and operation panel for inputting data required for an arithmetic operation unit 11 (see FIG. 3) corresponding to the powdered or granular materials to be measured their moisture content.

A communication pipe 7 communicates the vaporization treatment chamber 2 and the moisture measuring chamber 4 and includes an air purge means for blowing the dehumidified and dried air fed from the dehumidified and dried air supply means 1 into the vaporization treatment chamber 2 and the moisture measuring chamber 4 and for discharging the air from respective chambers to atmosphere. According to the moisture measuring apparatus A of the present invention, moisture measurement can be performed under more preferable conditions because atmospheric air can be prevented from entering and the vaporization treatment chamber 2 and the moisture measuring chamber 4 are kept under highly dry condition.

Further according to the moisture measuring apparatus A, an air source can be used commonly because a transport air for transporting sampled powdered or granular materials into the vaporization treatment chamber 2 can be supplied form the dehumidified and dried air supply means 1.

A rotary sampling apparatus for powdered or granular materials disclosed in U.S. patent application Ser. No. 07/859,004 and EPC Patent Application No. 92302657.9 can be employed as a sampling apparatus used for the on-line moisture measuring system of the present invention. When such a sampling apparatus is used, a fixed amount of sampled powdered or granular materials can be easily entrapped in the vaporization treatment chamber 2 only by appropriately supplying dehumidified and dried air from the moisture measuring apparatus A.

Figure 2:
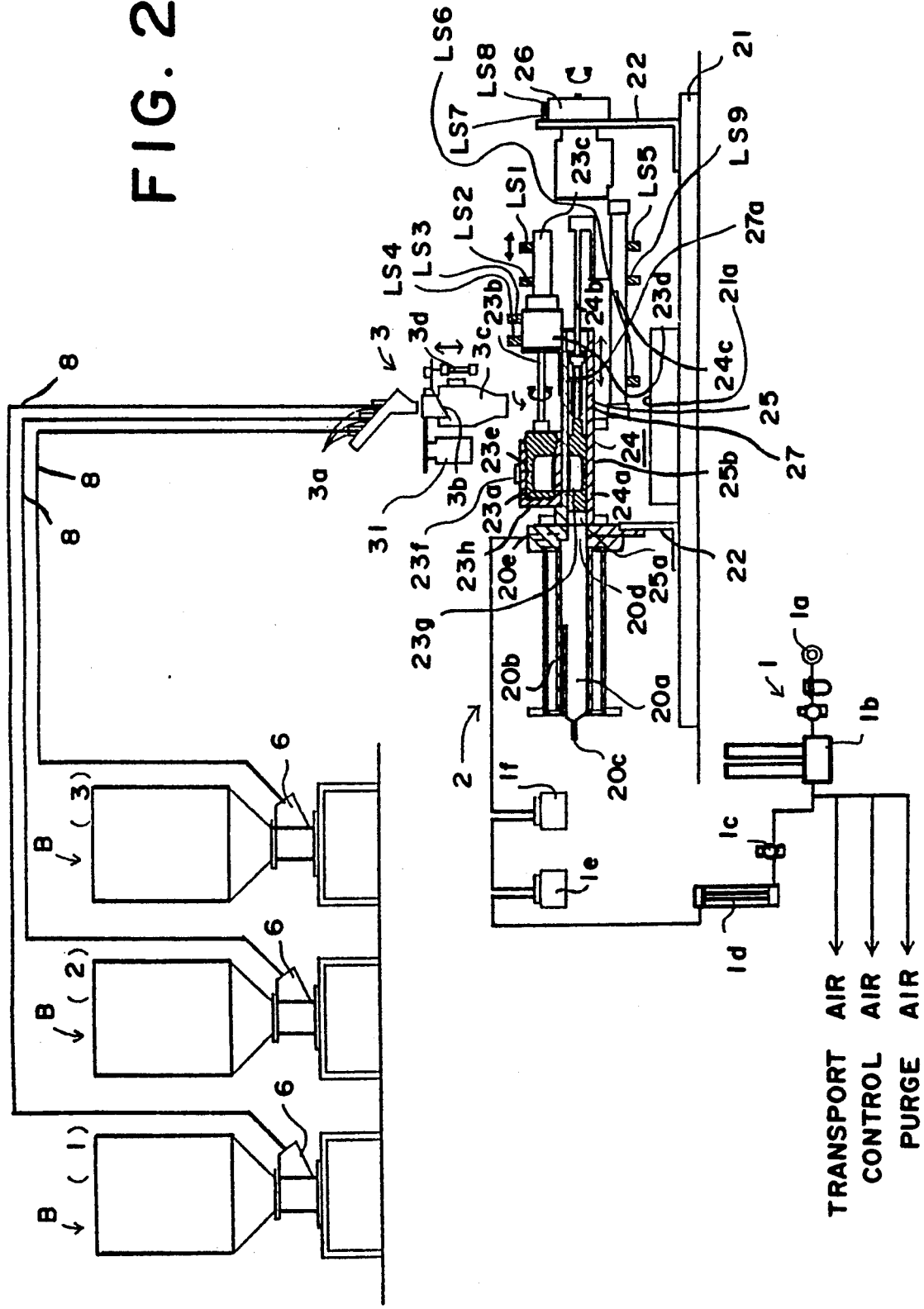
FIG. 2 shows a detailed construction of a vaporization treatment chamber and material weighing means of a moisture measuring apparatus according to the present invention.

FIG. 2 shows the vaporization treatment chamber 2 and the dehumidified and dried air supply means 1 in the moisture measuring apparatus A.

The top of the vaporization treatment chamber 2 is provided with the three sample ports 3a as the material insert ports corresponding to three hopper dryers B (#1)–(#3) which are storing containers for powdered or granular materials.

Material measuring means 3 is provided with a load cell 31 for weighing sampled pelletized resins. A cylindrical material insert chute 3c having a damper 3b, the pelletized resins on the damper 3b are weighed by the load cell 31, the damper 3b is opened by operating an air cylinder 3d, and the pelletized resins on the damper 3b fall down.

The vaporizer 20a is made of a heat-resistant glass and the like and it is served as a heating part by winding a heater 20b around its periphery. Nesa electrodes or Nichrome wires are used for the heater 20b. When Nesa electrodes are used, powdered or granular materials in the vaporization treatment chamber 2 can be seen, and also the body of the vaporization treatment chamber 2 can be made thin and compact. The vaporizer 20a is preferably heated and maintained at a temperature just before powdered or granular materials are dissolved in order to vaporize all the water contained in the powdered or granular materials. For this purpose, a temperature control apparatus (not shown) controls the vaporizer 20a to keep an appropriate temperature before the materials are received therein. A sample boat 24 having a receiver 24a is contained in a cylindrical body 25, an opening end 25a of which is provided for putting the sample boat 24 in and out and is connected with the vaporizer 20a.

The sample boat 24 is connected with a rod 24b of a second slide cylinder 24c and the receiver 24a of the sample boat 24 is freely put in and out of the vaporizer 20a through an opening 20d by sliding the cylinder 24c forward and backward. The sample boat 24 is controlled its insertion, withdrawal or discharge confirmation position by advancing or retreating operation of a first slide cylinder 23c and the sample boat 24 is provided with limit switches LS6, LS5 and LS9 to enable such a position control.

Figure 11:
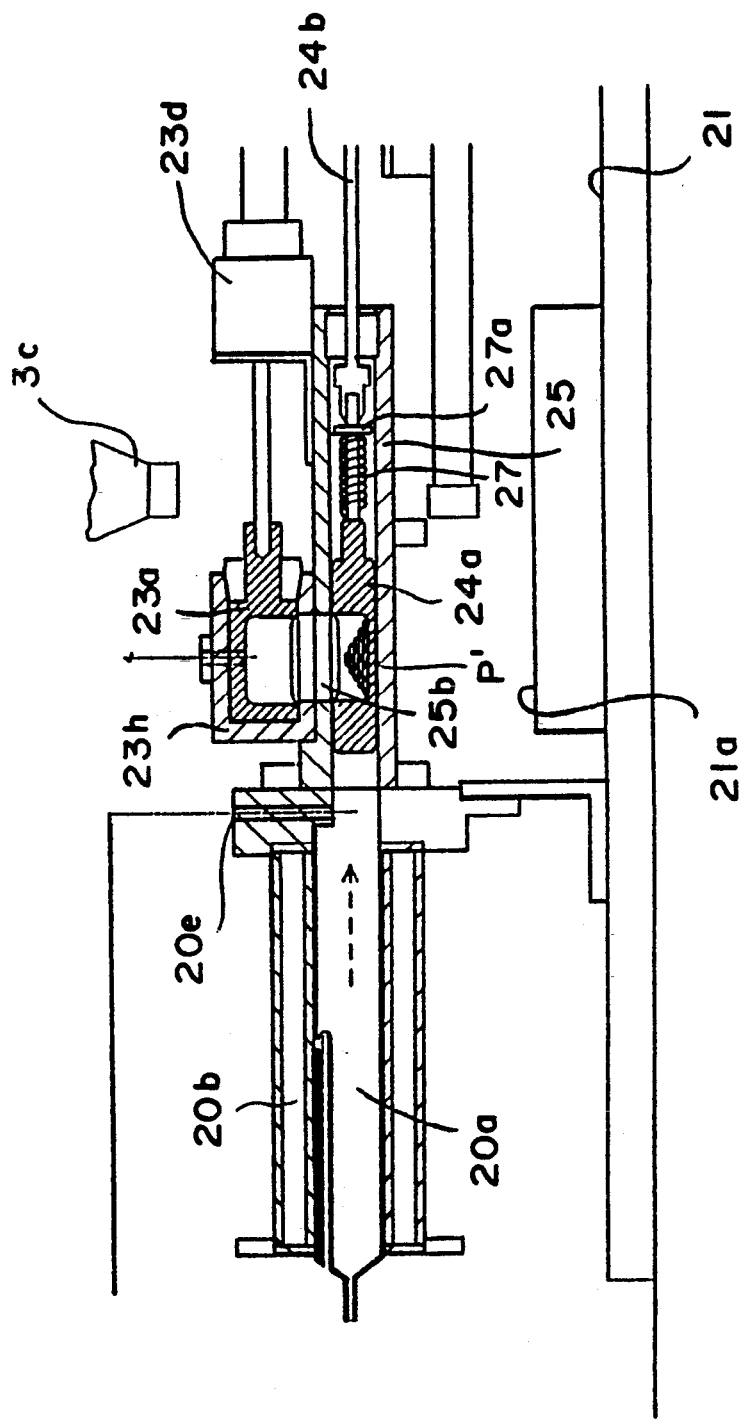
FIG. 11 is a vertical sectional view of a main part showing the positions of a sample boat and material transferring means when heated powdered or granular materials are taken out of a vaporizer to be cooled.
Figure 14:
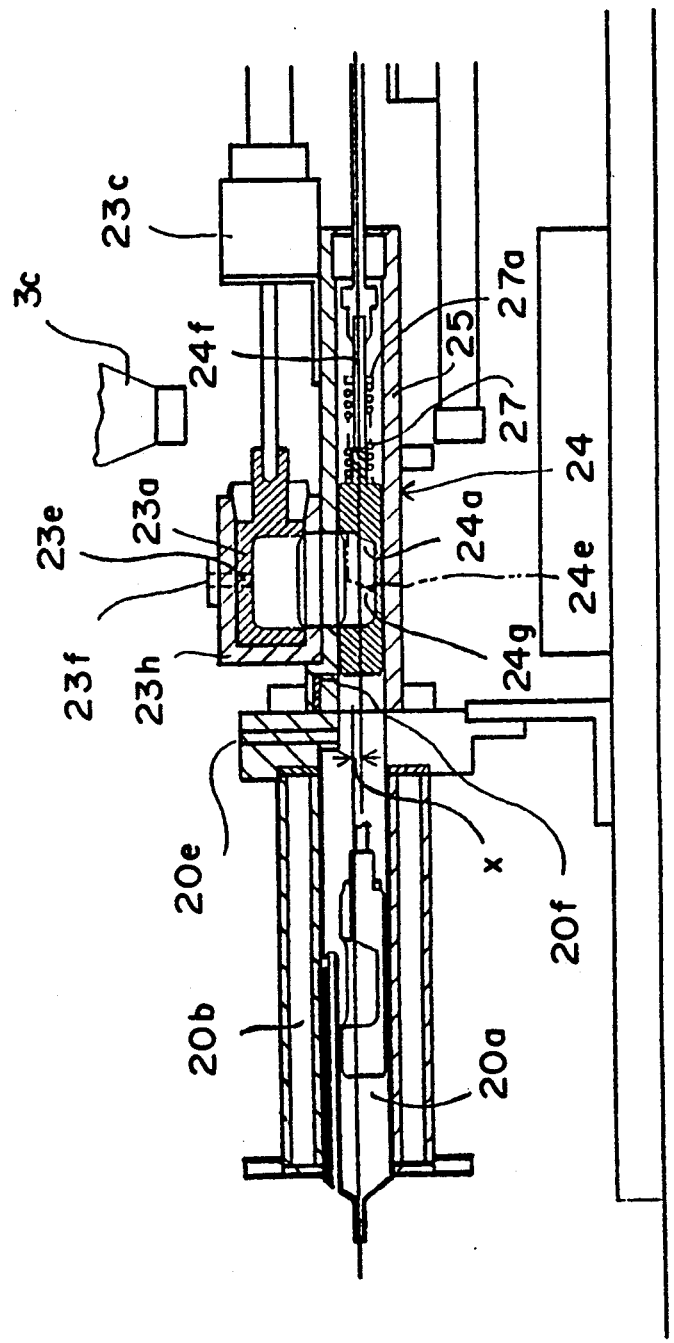
FIG. 14 is a vertical sectional view showing a sample boat.

FIG. 14 shows a detailed construction of the sample boat 24. The cylinder rod 24b is fixed with a scraper 24e at the initial end thereof and connected with a small rod 24f fitted with a spring 27 and a stopper ring 27a at its periphery. The sample boat 24 is constructed such that the scraper 24e can be put in and out of a material receiving space 24g of the vessel-like receiver 24a. The scraper 24e is kept retracting in the material receiving space 24g of the receiver 24a when the spring 27 is expanded as shown in FIG. 11. The central axis of the cylindrical body 25 containing the sample boat 24 is slightly and downwardly off-centered (x) with the central axis of the vaporizer 20a.

Figure 8:
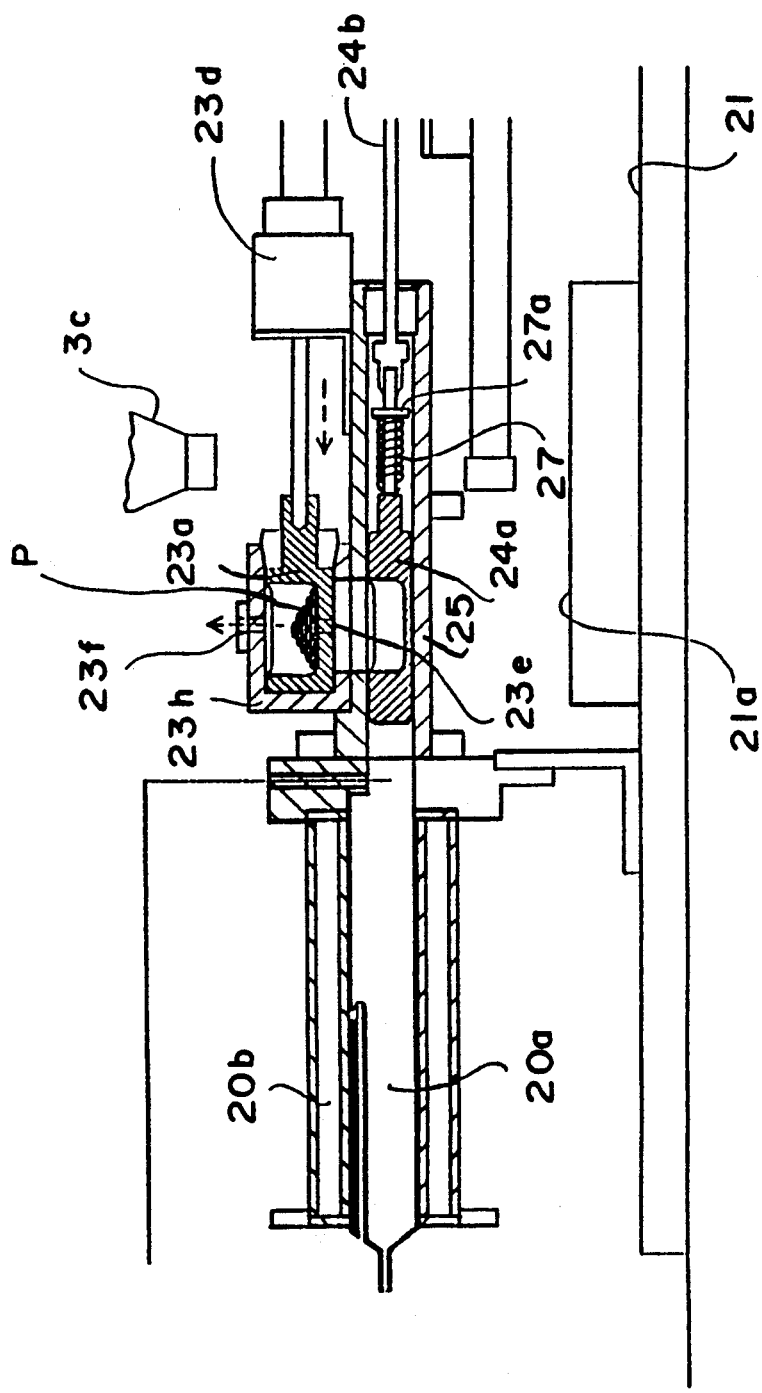
FIG. 8 is a vertical sectional view of a main part showing the positions of a sample boat and material transferring means when sampled powdered or granular materials receives a purged air.
Figure 9:
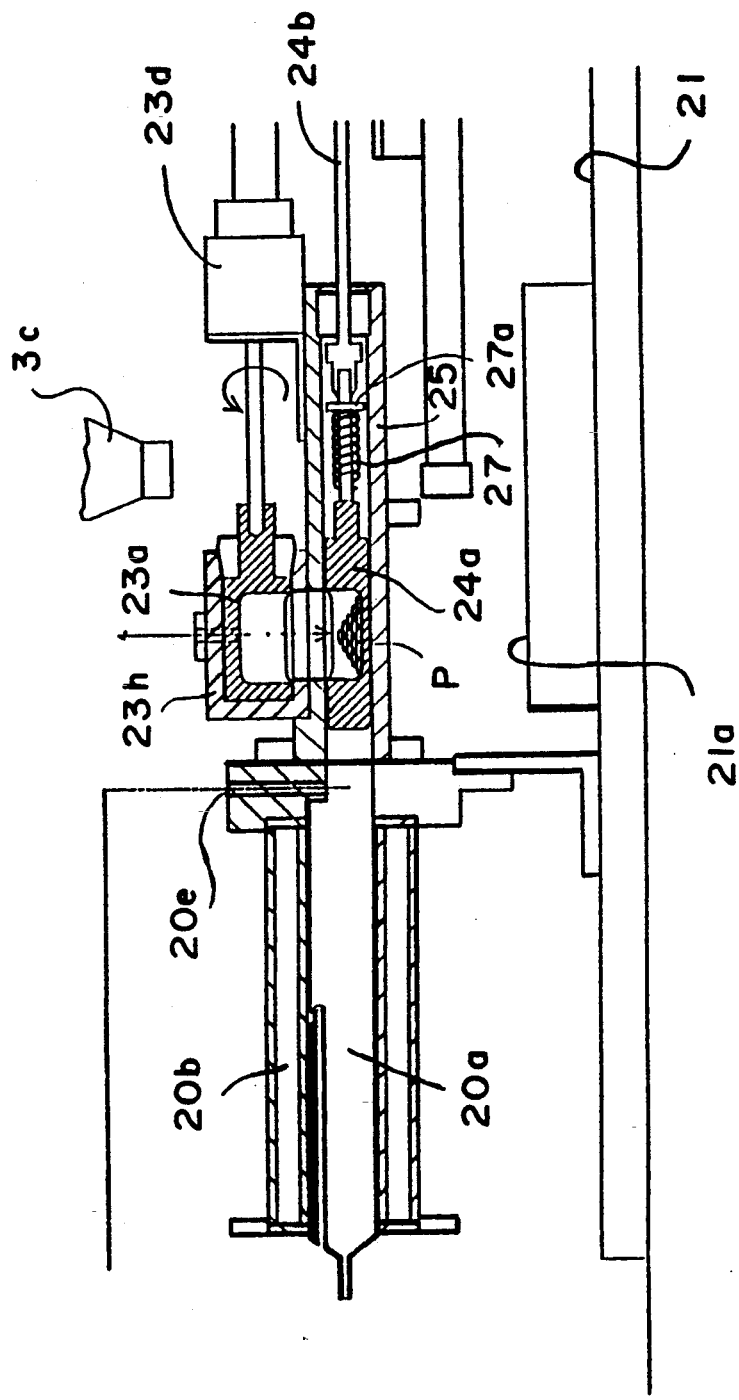
FIG. 9 is a vertical sectional view of a main part showing the positions of a sample boat and material transferring means when sampled powdered or granular materials are transferred to the sample boat from the material transferring means.
Figure 10:
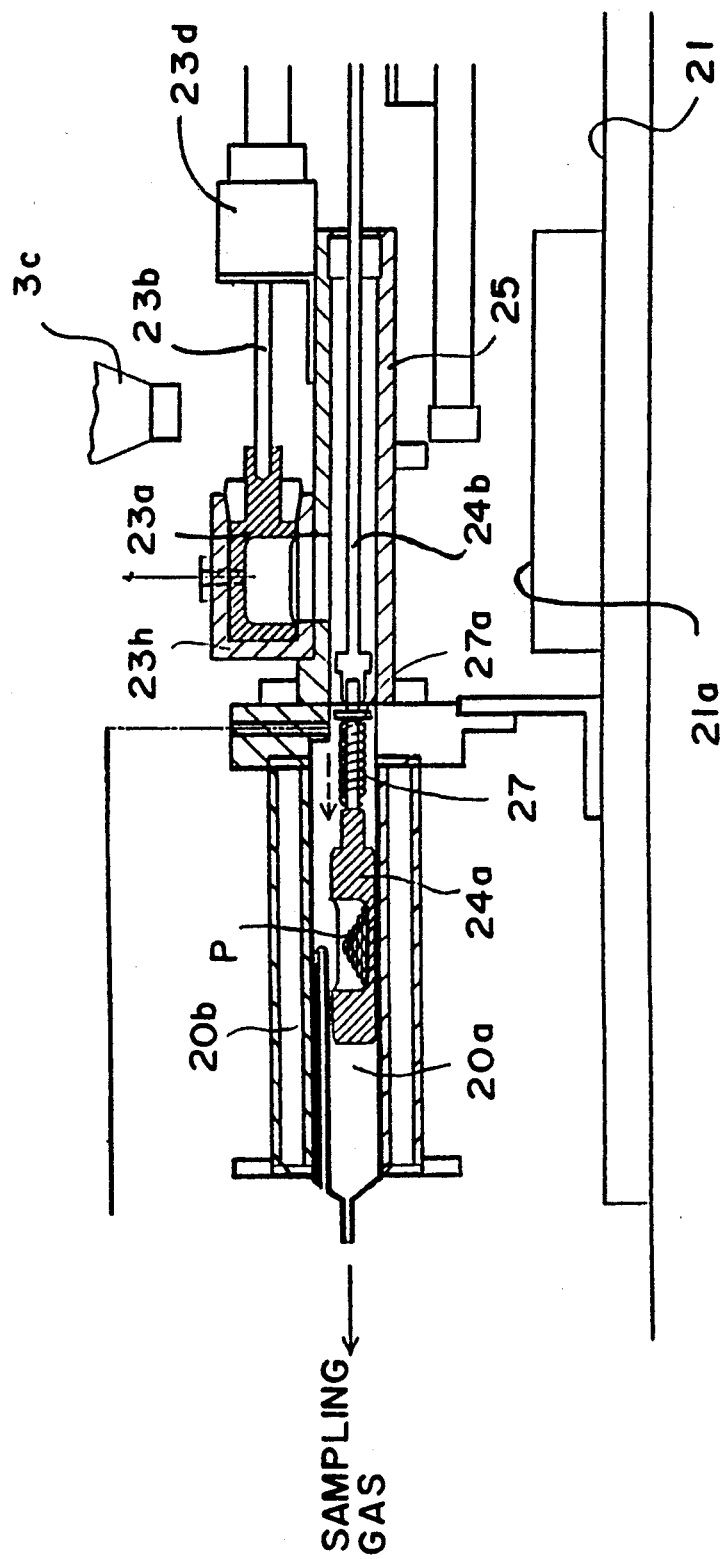
FIG. 10 is a vertical sectional view of a main part showing the positions of a sample boat and material transferring means when sampled materials are stored in a vaporizer.
Figure 12:
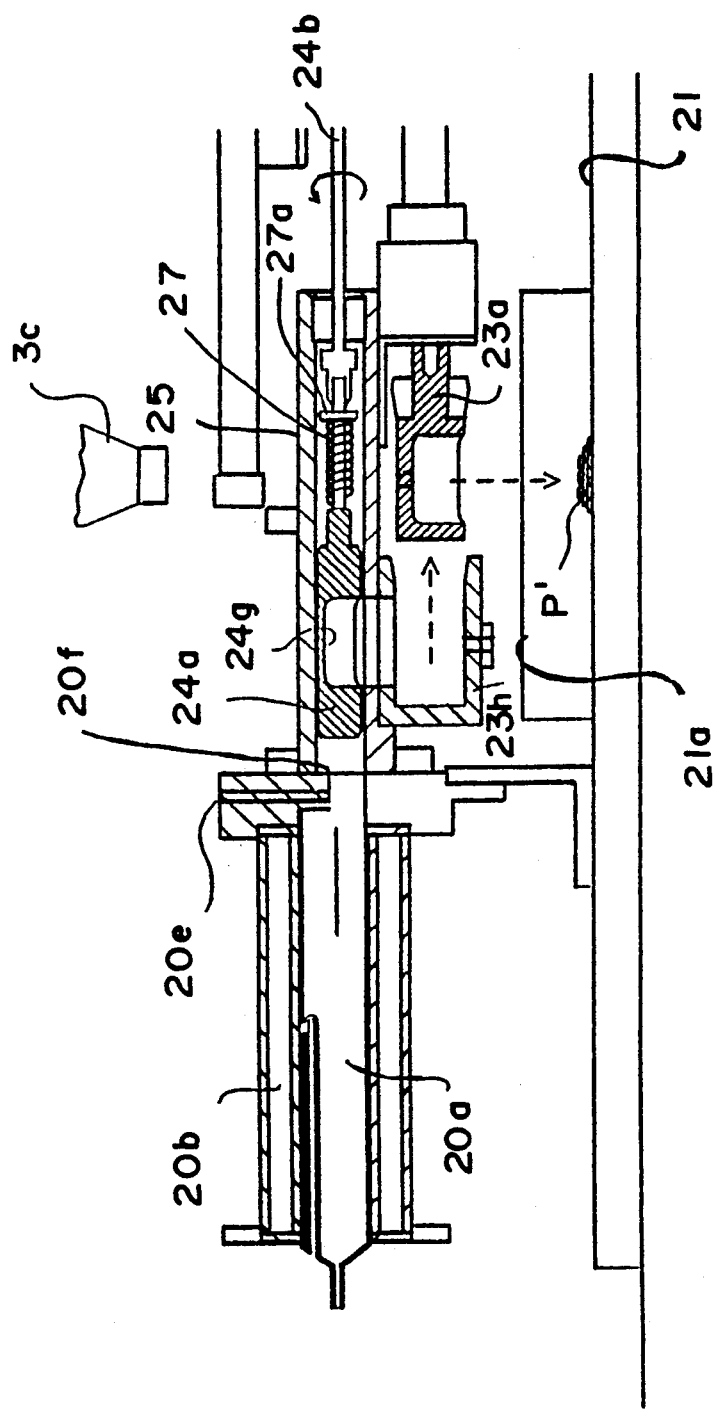
FIG. 12 is a vertical sectional view of a main part showing the positions of a sample boat and material transferring means when cooled powdered or granular materials are transferred into material transferring means.
Figure 13:
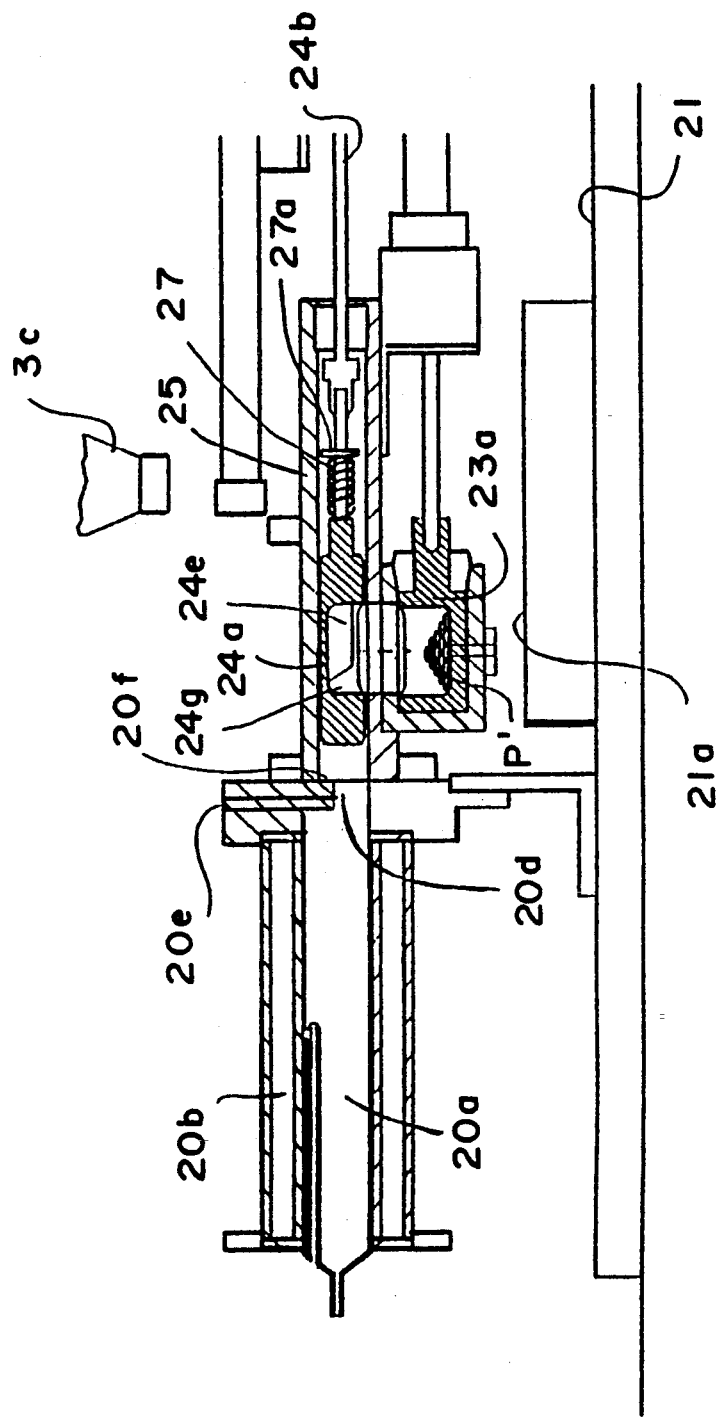
FIG. 13 is a vertical sectional view of a main part showing the positions of a sample boat and material transferring means when cooled powdered or granular materials are discharged.

The receiver 24a of the sample boat 24 can enter in the vaporizer 20a without any resistance when the cylinder rod 24b is forwarded, when material transferring means 23 is positioned over the sample boat 24 as shown in FIGS. 8–10. On the other hand, in a reverse condition such that the material transferring means 23 is positioned under the sample boat 24 as shown in FIGS. 12 and 13, the receiver 24a of the sample boat 24 can't enter in the vaporizer 20a even if the cylinder rod 24b is forwarded because the sample boat is obstructed by an upper wall 20f of an opening end of the vaporizer 20a.

At this time the spring 27 is contracted due to its elasticity and the scraper 24e is pushed by the spring 27. Then the scraper 24e projects out of the material receiving space 24g of the receiver 24a as shown in FIG. 12 and the scraper 24e scrapes off the powdered or granular materials adhered to the material receiving space 24g.

Figure 7:
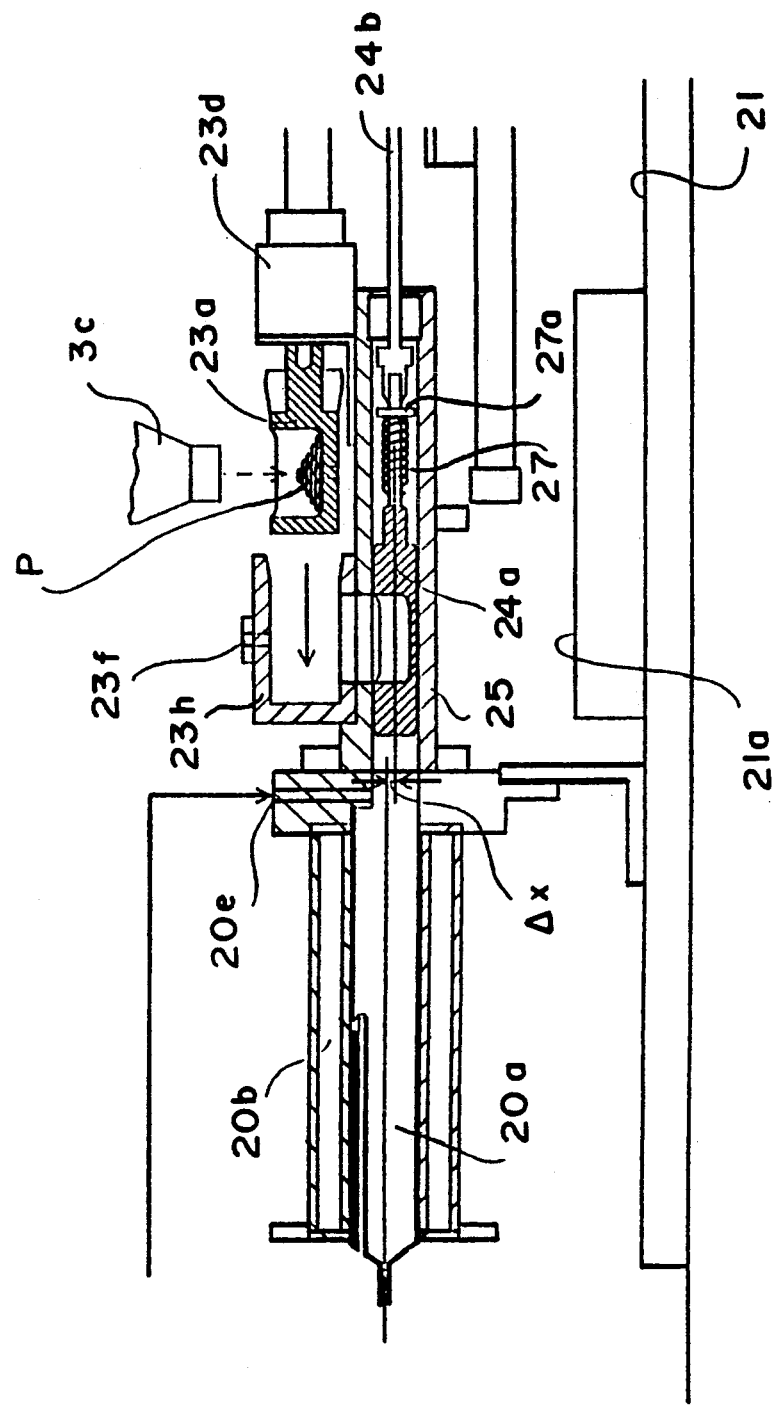
FIG. 7 is a vertical sectional view of a main part showing the positions of a sample boat and material transferring means when sampled powdered or granular materials are received from a material insert chute.

As shown in FIGS. 7, 8 and 9, the material transferring means 23 is provided over the cylindrical body 25 containing the sample boat 24. The material transferring means 23 receives pelletized resins fallen and inserted form the material insert chute 3c and transfer the pelletized resins to the receiver 24a of the sample boat 24. A cylinder rod 23b of the first slide cylinder 23c is connected at the rear of the material transport means 23. The numeral 23d indicates an air-operated first rotary actuator. The first slide cylinder 23c is designed to move the rod 23b back and forth and the first rotary actuator 23d is designed to rotate the rod 23b, whereby the receiver 23a of the material transferring means 23 can move back and forth and rotate up and down.

The material transferring means 23 is controlled to be positioned at a material receiving position, a material transfer position, a turn over position and a return position by sliding operation of the slide cylinder 23c and turning over operation of the first rotary actuator 23d. In order to enable such a positioning control the material transferring means 23 is provided with limit switches LS2, LS1 and LS3. (FIG. 2)

The cylindrical body 25 containing the vaporizer 20a and the sample boat 24 is fixed on a pedestal 21 with supports 22 and 22. The cylindrical body 25 is constructed such that it can be rotated separating from the vaporizer 20a by means of the second rotary actuator 26 provided at one support 22. For this purpose limit switches LS7 and LS8 are provided for detecting the turn over position and the return position of the second rotary actuator 26. The numeral 21a indicates a material disposal container provided on the pedestal 21.

The cylindrical body 25 and the material transferring means 23 are integrately fixed such that their vertical position is reversed when the second rotary actuator 26 is turned over, because the cylinder 23c is fixed on the cylindrical body 25. (See FIG. 12)

As shown in FIG. 11, a material receiving port 25b is provided at the top of the cylindrical body 25 and a cover 23h for sliding the material transferring means 23 is formed so as to cover the material receiving port 25b.

The material transferring means 23 reciprocates between the material insert chute 3c and the cover 23h. By such an operation, the material transferring means 23 receives the pelletized resins fallen from the material insert chute 3c in the receiver 23a thereof, moves into the cover 23h, delivers the pelletized resins to the receiver 24a of the sample boat 24 by turning over. Thus, transference of the pelletized resins is accomplished. For this purpose, the first cylinder 23c and the first rotary actuator 23d are constructed so as to rotate and slide the material transferring means 23 by means of the rod 23b.

A carrier gas transport pipe (not shown) is connected at the tip 20c of the vaporizer 20a for feeding the vapor generated in the vaporizer 20a to the moisture meter 41 in the moisture measuring chamber 4 together with a carrier gas.

The dehumidified and dried air supply means 1 includes an air supply source 1a, heats and dehumidifies the air supplied from the air supply source 1a so as to have a low dew point (for example, from −70 degrees centigrade to −40 degrees centigrade), and sends the air.

Air supplied from the air supply source 1a such as a compressor is dehumidified by a heatless dryer 1b so as to satisfy a fixed level of a dew point, measured the supply pressure and the flow amount thereof by a regulator 1c and an air flow meter 1d, and supplied to the vaporizer 20a from a carrier gas introduction port 20e through moisture absorbers 1e and 1f. The dehumidified and dried air thus supplied to the vaporizer 20a is fed to the moisture meter 41 together with the vapor generated by heating the pelletized resins in the sample boat 24.

The air supply means 1 can divergently use the air dehumidified and dried by the heatless dryer 1b as a transport air for sampling, a control air for the slide cylinders and the actuators, and a purge air for the air purge means.

The cover 23h containing the receiver 23a of the materials transport means 23 is provided with a hole 23f corresponding to a hole 23e formed at the top of the receiver 23a. When the material transferring means 23 delivers the pelletized resins received from the material insert chute 3c to the receiver 24a of the sample boat 24, air exchange is performed by blowing a carrier gas toward outside through the holes 23e and 23f.

The moisture measuring chamber 4 receives vapor supplied from the vaporizer 20a together with a carrier gas, as shown in FIG. 1, measures the water quantity of the materials by means of a Karl Fischer reagent.

In this embodiment, the moisture meter 41 employs a colorimetric measuring method. A container 42 storing a Karl Fischer reagent and a container 43 containing methanol used as a thinner are connected with a liquid container 41a including an agitating motor (not shown) through tubes 42a and 43a respectively so that these liquids are automatically supplied respectively. A light projector and a light receiver (both are not shown in figures) are provided at each side of the liquid container 41a through optical fibers. The moisture quantity of the materials are measured by measuring absorptivity of the solution stored in the liquid container 41a when light is projected into the liquid container 41a from the projector and received in the receiver. The liquid container 41a is constructed such that the solution is automatically exchanged and a new reagent is supplied when the solution reaches its measuring limitation, because the absorptivity of the solution declines accompanying the increase of the water supplied from the vaporizer 20a.

A trace-moisture measuring apparatus employing a Karl Fischer reagent such as Mitsubishi Karl Fischer Moisture Meters (for example, CA-03, CA-06 and CA-10) can be used as the moisture meter 41 in the moisture measuring chamber 4. With such a meter, an accurate moisture measurement is accomplished only by introducing the water in the form of a vapor by heating pelletized resins together with the carrier gas.

Figure 3:
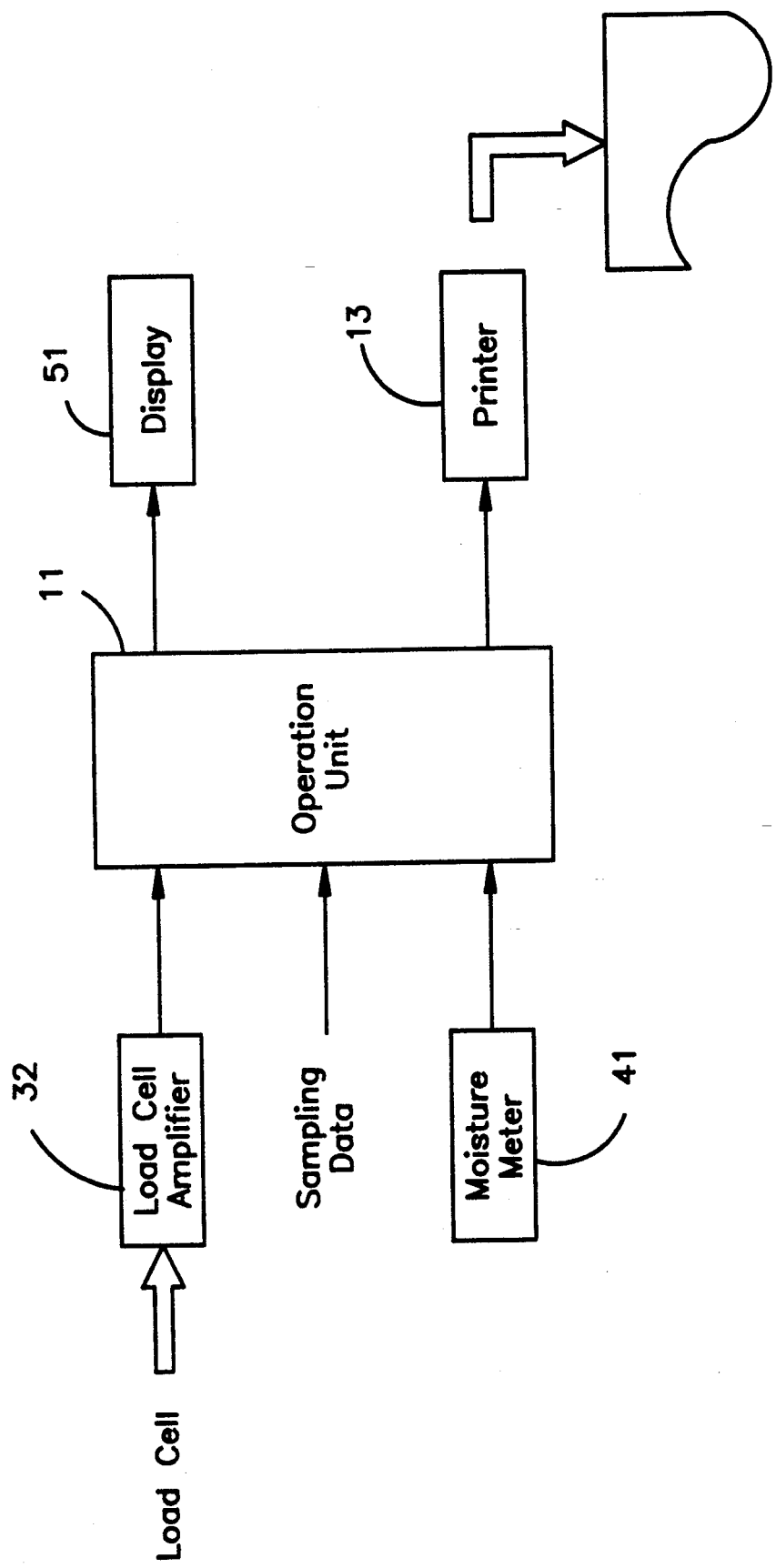
FIG. 3 is a block diagram showing construction of an arithmetic operation unit.

FIG. 3 shows a construction of the operation unit 11. The water quantity measured by the moisture measurement unit 41 and the weight value (data) measured by the material measuring means 3 and output by a load cell amplifier 32 are sent to the operation unit 11 together with sample data such as sampling date and time and a sample port number. Then the moisture content is calculated in the operation unit 11 and the calculated value can be displayed on the display 51 of the display/operation panel 5, and printed out at a printer 13, as necessity requires, after the classified total is computed.

Thus, the operation unit 11 calculates data sent from the moisture meter 41, data sent from the load cell amplifier 32 of the material measuring means 3, and the sampling data, then the calculated result is displayed on the display 51 after the heat treatment of the pelletized resins is finished.

Next, constructions and operations of the control unit of the present invention are explained.

Figure 4:
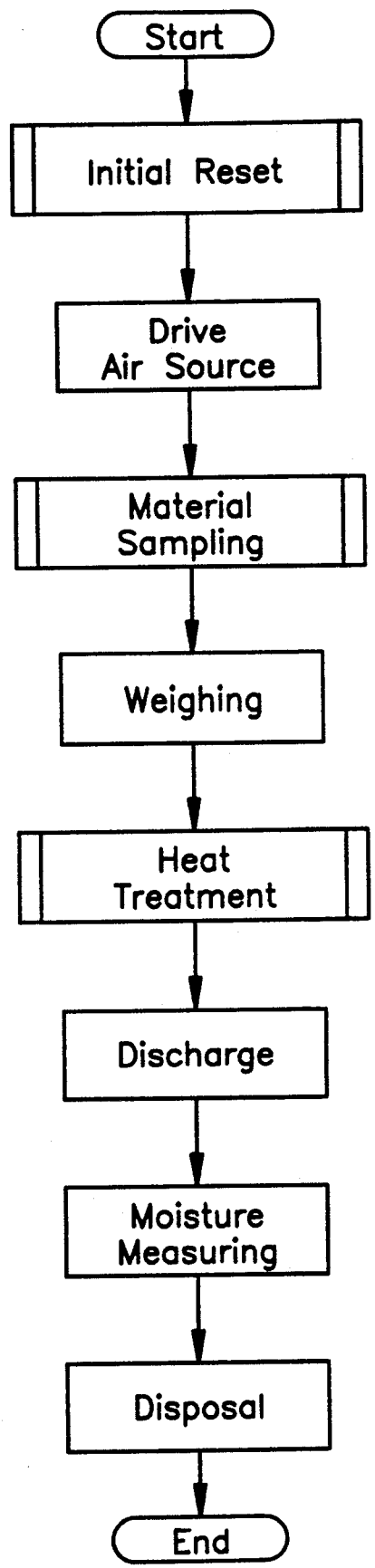
FIG. 4 is a flow chart of on-line control operations according to the present invention.

FIG. 4 shows a basic operation of the moisture measuring apparatus A according to the present invention. According to the present invention, a series of operations such as sampling of powdered or granular materials, moisture measuring by heat treatment and discharging of the heated materials can be performed automatically as shown in the figure. All means and instruments are set at a pre-stage, in which control operations aren't started, at the time of first initial reset. Then the air supply source is driven, powdered or granular materials are automatically sampled, their weight is measured, and they are heated in the vaporizer 20a while being supplied with a dehumidified and dried air. The vapor generated from the sampled powdered or granular materials is supplied to the moisture meter 41 and the moisture quantity of the materials is measured by means of a Karl Fischer reagent in the moisture meter 41. The moisture quantity and the weight value of the materials are input into the operation unit 11 and the moisture content is calculated. Finally, the materials heated in the vaporizer 20a are automatically discharged and disposed of.

Figure 5:
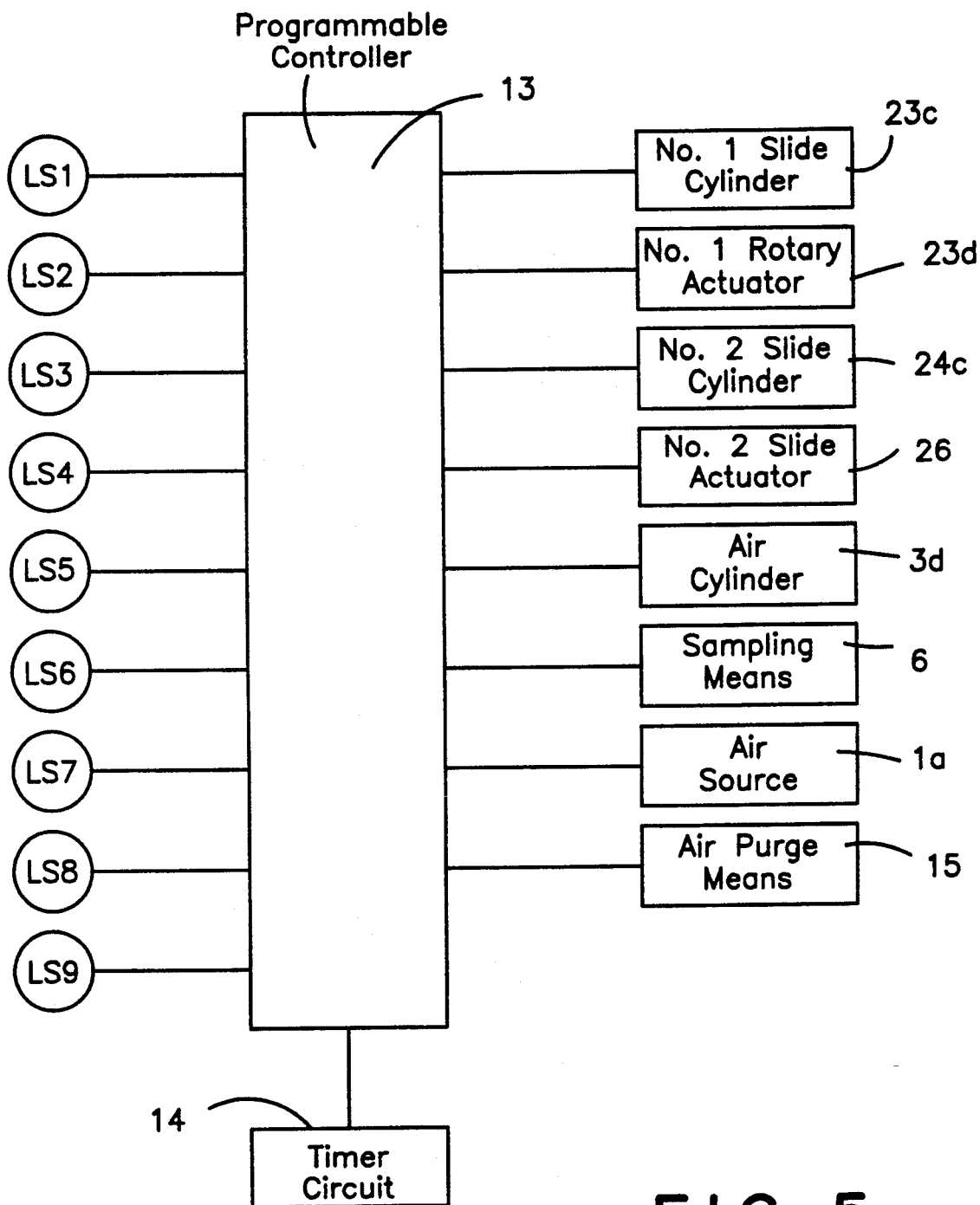
FIG. 5 is a block diagram of a control unit.

FIG. 5 shows a block diagram of a control unit when the apparatus of the present invention as shown in FIG. 2 is full-automatically operated.

In the figure, an on-line control is performed by a program controller 13. The programmable controller 13 sequentially controls driving operations of the air supply source 1a, the sampling means 6, air purge means 15 for the air purge means, the air cylinder 3d for opening the damper 3b of the material insert chute 3c, the first and the second slide cylinders 23c and 24c, and the first and the second rotary actuators 23d and 26 corresponding to the operations of limit switches LS1–LS9. The numeral 14 is a timer circuit.

Figure 6:
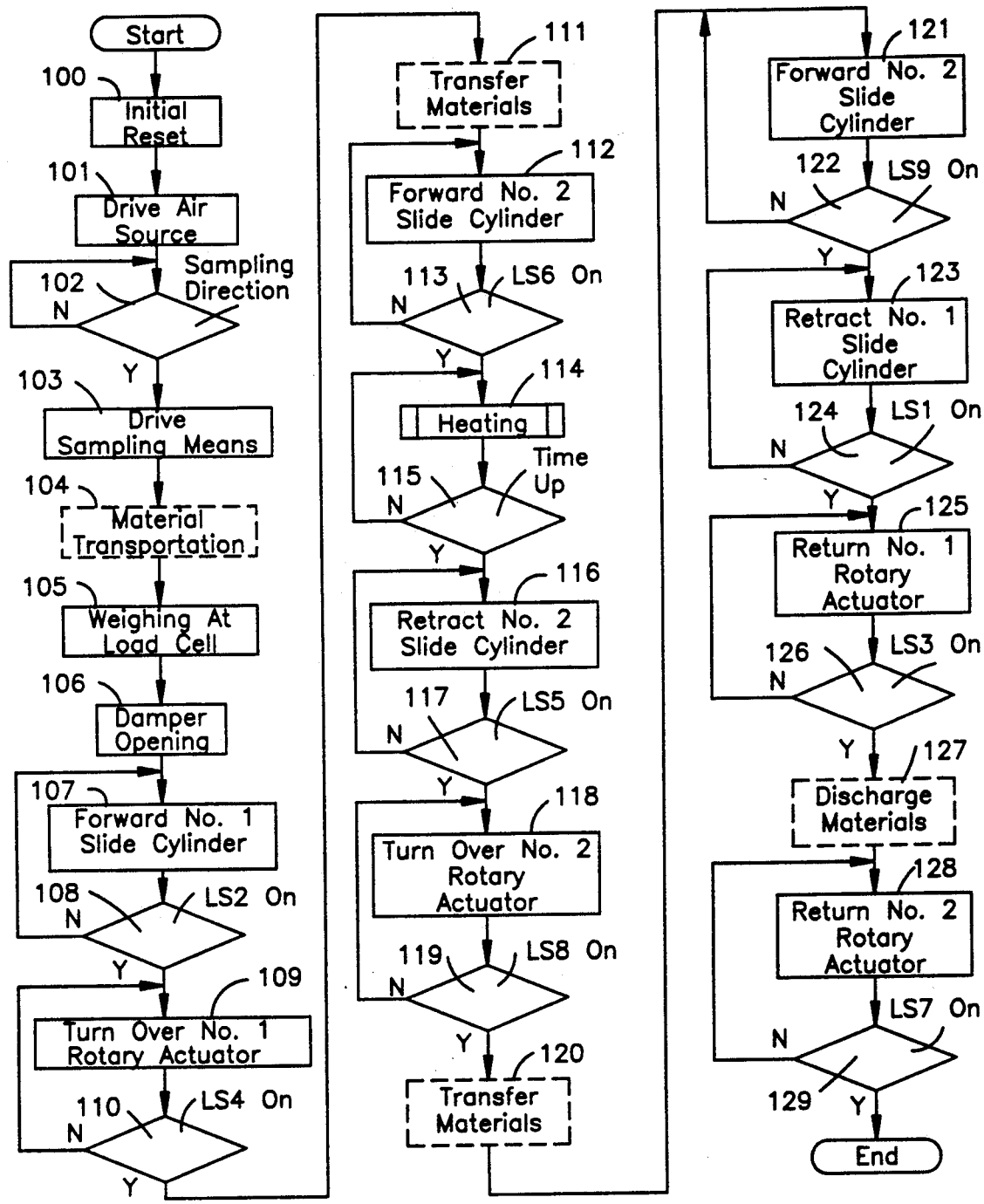
FIG. 6 is a flow chart showing control operations of a control unit.

FIG. 6 is a flow chart showing the steps 100–129 of control operations. An initial reset is executed, the air supply means is driven, sampling indication is received by the controller 13, and dehumidified and dried air is supplied from the dehumidified and dried air supply means 1 to the sampling means 6. A fixed amount of pelletized resins is pneumatically transported from the sampling means 6 to the material insert chute 3c through the material insert port 3a provided at the top of the material measuring apparatus A, the weight of the materials is measured by the load cell 31, and the damper 3b of the material insert chute 3c is opened. (steps 100–106) In this time, the receiver 23a of the material transferring means 23 is positioned directly under the material insert chute 3c, therefore, the pelletized resins P inserted from the material insert chute 3c can be received in the receiver 23a of the material transferring means 23. (FIG. 7)

The first slide cylinder 23c is forwarded and the receiver 23a having the sampled pelletized resin P is contained in the cover 23h. Then the limit switch LS2 is turned on. At this time, replacement of air is performed by a carrier gas for preventing outside air from entering.

The carrier gas supplied from the carrier gas introduction port 20e of the vaporizer 20a is introduced in the vaporizer 20a, the cylindrical body 25, and the receiver 23a. The carrier gas drives out the air remaining in them and is discharged outside from the air release hole 23f. (one-dotted arrows in FIG. 8)

Then, the first actuator 23d is driven, the receiver 23a is turned over, and the pelletized resins fall through the material receiving port 23g. The first rotary actuator 23d keeps turning over until the limit switch LS4 is turned on. The sample boat 24 is disposed in the cylindrical body 25 with its receiver 24a aligning the material receiving port 25b and the pelletized resins P fallen from the receiver 23a of the material transferring means 23 are received in the receiver 24a of the sample boat 24, whereby the material are transferred. (steps 107–111 and FIG. 9)

After the receiver 24a of the sample boat 24 thus receives the pelletized resins P, the second slide cylinder 24c is forwarded until the limit switch LS6 is turned on, and the receiver 24a is inserted into the vaporizer 20a to be heated therein. The pelletized resins P are heated for a time necessary for extracting almost all of the vapor contained in the resin P. The time is measured by the timer circuit 14. (steps 112–115)

The vapor generated from the pelletized resins P during heat treatment is supplied to the moisture meter 41 of the moisture measuring chamber 4 through a transport pipe as a sample gas together with the carrier gas introduced from the dehumidified and dried air supply means 1. (FIG. 10)

The moisture meter 41 introduces the carrier gas supplied with the vapor from the vaporizer 20a into the liquid container 41a and measures the water quantity of the materials by the change of absorptivity caused by the reagent being thinned. The measured result is sent to the operation unit 11 together with the weight value (data) output from the load cell amplifier 32 of the material weighing means 3 and the operation unit 11 calculates the moisture content of the materials. After the pelletized resins P are heated for a fixed time in the vaporizer 20a, the hardened pelletized resins P' left in the receiver 24a of the sample boat 24 are discharged in a following manner.

The second slide cylinder 24c is retracted until the sample boat 24 containing the heated pelletized resins P' reaches the position where the receiver 24a meets a material receiving port 25d. The position is detected by the limit switch LS5 and the second slide cylinder 24c is stopped when the limit switch LS5 is turned on. (steps 116–117) The sample boat 24 is left at this position for a fixed time and the pelletized resins in the receiver 24a are cooled. The cooling time is measured by the timer circuit 14 following the control program of the programmable controller 13. (See FIG. 11)

At this time, the receiver 23a of the material transferring means 23 is still kept in the cover 23h and the material transferring means 23 keeps discharging the carrier gas introduced in the vaporizer 20a from the gas release hole 23f in order to prevent outside air from entering.

After the pelletized resins P' are thus cooled for a fixed time, the second rotary actuator 26 is rotated. The rotation is detected by the limit switch LS8 and the rotary actuator 26 stops rotating when the limit switch LS8 is turned on. (Steps 118, 119)

As a result, the up-and-down position of the sample boat 24 and the material transferring means 23 is reversed. Then, the second slide cylinder 24c is forwarded and the scraper 24e provided in the receiver 24a of the sample boat 24 is projected. (at this time the receiver 24a doesn't move) The hardened pelletized resins P' are scraped by the scraper 24e even if they are adhered in the receiver 24a and received in the receiver 23a of the material transferring means 23. (FIG. 12 and steps 118–120)

After the pelletized resins P' in the receiver 24a of the sample boat 24 are thus received in the receiver 23a of the material transferring means 23, the first slide cylinder 23c is retracted until the limit switch LS1 is turned on. Then the first rotary actuator 23d is returned to the normal style from the turned-over style until the limit switch LS3 is turned on. As a result, the material transferring means 23 is repositioned under its waiting position, the pelletized resins P' fall from the receiver 23a of the material transferring means 23, and they are discharged in the material disposal container 21a provided on the pedestal 21. (FIG. 13, steps 121–127)

After the material transferring means 23 is thus returned under its original waiting position, the rotary actuator 26 is rotated and the material transferring means 23 is repositioned its original position, whereby all means and parts are returned to their original reset positions. (steps 128–129)

According to the present invention, pelletized resins are sampled, the sampled resins are heated, their water quantity is measured, and they are disposed. Such a serial operation is repeatedly performed, whereby the moisture content of the materials can be measured promptly and repeatedly without using manpower.

The moisture measuring apparatus of the present invention can perform a series of operations unattended wherein powdered or granular materials are heated, the moisture content of the materials is measured, and they are disposed each time materials are sampled.

Because cheap air is used as a carrier gas for Karl Fischer reaction displacing a costly nitrogen gas in the present invention, its running cost becomes cheap. And its maintenance can be facilitated because exchange of gas cylinder isn't required.

Further, the vaporization treatment chamber 2 and the moisture measuring chamber 4 are kept in dried condition when the present invention is provided with the air purge means, therefore a more accurate moisture measurement is accomplished.

Furthermore, when transportation of the sample of powdered or granular materials is performed by a dehumidified and dried air supplied from the dehumidified and dried air supply means 1 in the moisture measuring apparatus A, construction of the moisture measuring system can be simplified and the sampled materials don't absorb moisture while being transported.

What is claimed is:

1. An on-line type moisture measuring system for powdered or granular materials, comprising:

sampling means designed to be attached to a material storage container storing powdered or granular materials, for sampling a fixed amount of the materials and for pneumatically transporting the sampled materials;

dehumidified and dried air supply means having an air supply source, for generating dehumidified and dried air by heating and dehumidifying the air supplied from said air supply source;

material weighing means for weighing the sampled materials fed from said sampling means;

a vaporization treatment chamber including a sample boat for receiving the weighed materials by said material weighing means and an airtight vaporizer having a heater for heating the weighed materials received in said sample boat while receiving the dehumidified and dried air supplied from said dehumidified and dried air supply means as a carrier gas;

a moisture measuring chamber having a moisture meter for measuring the water quantity of the weighed materials by the reaction of a Karl Fischer reagent by receiving the vapor generated in said vaporizer together with said carrier gas; and an arithmetic operation unit for calculating the moisture content of the sampled and weighed materials based on the moisture quantity measured by said moisture measuring chamber and the weight value weighed by said material measuring means;

whereby a fixed amount of powdered or granular materials sampled from said material storage container is repeatedly supplied each time sampled materials are treated in said vaporization treatment chamber so as to get the moisture content of the sampled materials.

2. An on-line type moisture measuring system as set forth in claim 1, further comprising:

a communication passage communicating said vaporization treatment chamber and said moisture measuring chamber; and an air purge means for outwardly purging the dehumidified and dried air supplied from said dehumidified and dried air supply means from both said vaporization treatment chamber and said moisture measuring chamber.

3. An on-line type moisture measuring system as set forth in claim 1, wherein transportation of the sampled materials into said vaporization treatment chamber is performed by the dehumidified and dried air supply from said dehumidified and dried air supply means as a transport air.

4. An on-line type moisture measuring system as set forth in claim 2, wherein transportation of the sampled materials into said vaporization treatment chamber is performed by the dehumidified and dried air supplied from said dehumidified and dried air supply means as a transport air.

* * * * *

UNITED STATES PATENT AND TRADEMARK OFFICE
CERTIFICATE OF CORRECTION

PATENT NO. : 5,301,440
DATED : April 12, 1994
INVENTOR(S) : Motoharu Shimizu et al It is certified that error appears in the above-identified patent and that said Letters Patent is hereby corrected as shown below:

Claim 3, column 12, line 16, "supply" should be --supplied--.

Signed and Sealed this

Twentieth Day of September, 1994

Attest:

BRUCE LEHMAN

Attesting Officer        Commissioner of Patents and Trademarks